(12) United States Patent
Hinchliffe et al.

(10) Patent No.: US 10,864,094 B2
(45) Date of Patent: Dec. 15, 2020

(54) FATIGUE-RESISTANT FLOW REGULATING DEVICE AND MANUFACTURING METHODS

(71) Applicant: Deep Vein Medical, Inc., Canton, MA (US)

(72) Inventors: Peter W. J. Hinchliffe, Campbell Hall, NY (US); Menno Kalmann, Elspeet (NL); Adam I. Lehman, Northford, CT (US); Olga Laksin, Boonton, NJ (US)

(73) Assignee: Deep Vein Medical, Inc., Canton, MA (US)

( * ) Notice: Subject to any disclaimer, the term of this patent is extended or adjusted under 35 U.S.C. 154(b) by 376 days.

(21) Appl. No.: 15/795,564

(22) Filed: Oct. 27, 2017

(65) Prior Publication Data

US 2018/0303638 A1    Oct. 25, 2018

Related U.S. Application Data

(62) Division of application No. 13/635,589, filed as application No. PCT/US2011/027724 on Mar. 9, 2011, now Pat. No. 9,801,737.

(60) Provisional application No. 61/314,699, filed on Mar. 17, 2010.

(51) Int. Cl.
| | |
|---|---|
| *A61F 2/82* | (2013.01) |
| *A61F 2/24* | (2006.01) |
| *A61L 27/04* | (2006.01) |
| *A61L 27/48* | (2006.01) |

(52) U.S. Cl.
CPC .............. *A61F 2/82* (2013.01); *A61F 2/2475* (2013.01); *A61L 27/047* (2013.01); *A61L 27/48* (2013.01); *A61L 2400/16* (2013.01); *Y10T 156/1051* (2015.01)

(58) Field of Classification Search
None
See application file for complete search history.

(56) References Cited

U.S. PATENT DOCUMENTS

| | | | |
|---|---|---|---|
| 2002/0055772 A1 | 5/2002 | McGuckin et al. | |
| 2002/0178570 A1* | 12/2002 | Sogard ................ | A61F 2/07 29/516 |
| 2003/0209835 A1 | 11/2003 | Chun et al. | |
| 2004/0167619 A1 | 8/2004 | Case et al. | |
| 2004/0260389 A1 | 12/2004 | Case et al. | |
| 2007/0093887 A1 | 4/2007 | Case et al. | |
| 2007/0288086 A1 | 12/2007 | Kalmann et al. | |
| 2009/0177269 A1 | 7/2009 | Kalmann et al. | |
| 2010/0057191 A1 | 3/2010 | Pavcnik et al. | |
| 2010/0256743 A1* | 10/2010 | Hinchliffe ........... | A61F 2/2418 623/1.24 |

OTHER PUBLICATIONS dictionary.com definition of shaping (Year: 2020).*
International Search Report and Written Opinion for PCT/US2011/027724 dated Nov. 30, 2011.

* cited by examiner

*Primary Examiner* — Barbara J Musser
(74) *Attorney, Agent, or Firm* — Brown Rudnick LLP; Thomas C. Meyers

(57) ABSTRACT

The subject invention is directed to devices and methods for producing devices for regulating blood flow in the venous system. In particular, the invention provides for artificial valves designed to regulate the flow of blood in human vessels, wherein such artificial valves include superior properties including fatigue resistance, biocompatibility, and ease of manufacture.

7 Claims, 12 Drawing Sheets

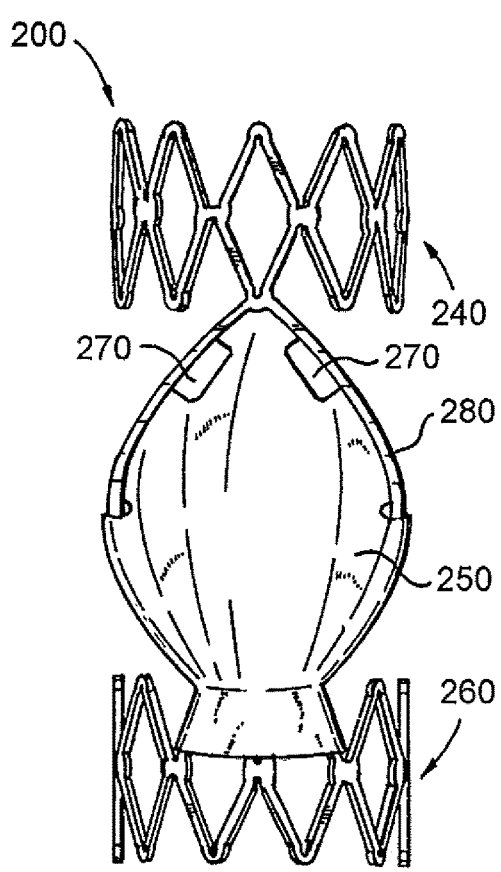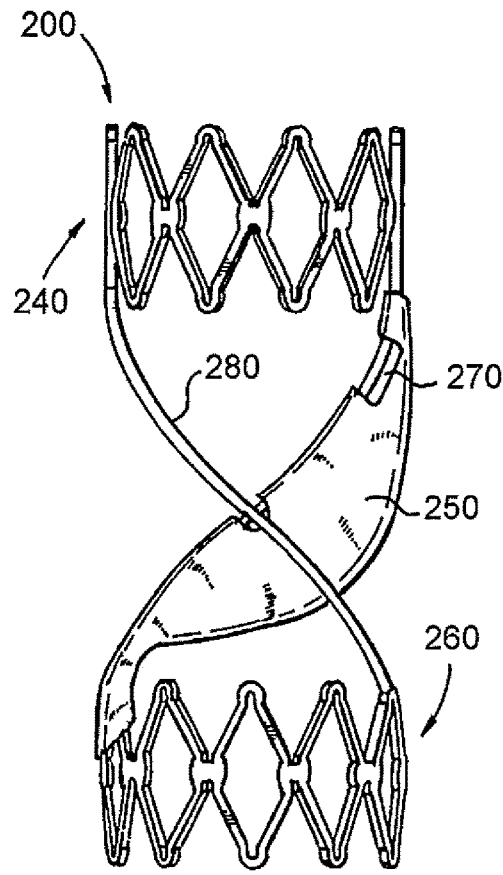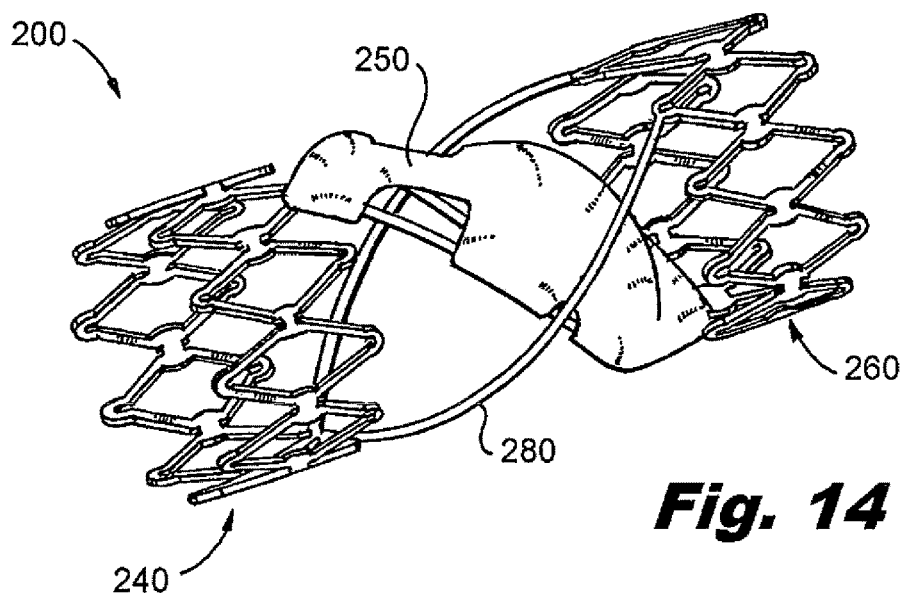

FATIGUE-RESISTANT FLOW REGULATING DEVICE AND MANUFACTURING METHODS

CROSS-REFERENCE TO RELATED APPLICATIONS

This application is a divisional of U.S. application Ser. No. 13/635,589, now U.S. Pat. No. 9,801,737, filed Dec. 27, 2012, which is a national stage entry of PCT/US2011/027724, with an international filing date of Mar. 9, 2011, which claims priority to U.S. Provisional Patent Application No. 61/314,699, filed Mar. 17, 2010, the entire contents of each of which are incorporated by reference herein in their entireties. This application incorporates by reference herein each of the following commonly assigned U.S. patent applications in its entirety: application Ser. No. 12/713,476 filed Feb. 26, 2010, application Ser. No. 12/319,176 filed Jan. 2, 2009, application Ser. No. 11/801,691 filed May 10, 2007, and application Ser. No. 11/801,489 filed May 10, 2007.

BACKGROUND OF THE INVENTION

1. Field of the Invention

The subject invention is directed to devices for regulating blood flow in the venous system, and more particularly, to the design and production of artificial valve devices designed to regulate the flow of blood in human vessels.

2. Description of Related Art

Artificial venous valves offer numerous possibilities that can be very attractive to clinicians and patients. Benefits of such designs include, the possibility of improved functional stability and life while reducing size and bulk of the valve, which offers opportunities for interventional, less traumatic procedures for valve placement. In spite of the existence of a great number of artificial valve designs, very few of them have managed to pass through clinical trials and make it to the clinical arena.

Today's use of artificial valves is limited to relatively bulky mechanical valves or tissue based valves. The reason for this is that small and compact valves, suitable for interventional applications, require the use of thin metal frames and ultra thin polymer parts joined together, to meet the harsh requirements of a multimillion cycle application in blood flow. Herein is the main problem of percutaneously inserted valves—their mechanical designs, historically, have not proven to be as robust as that of bulkier valves, and have been prone to biocompatibility, long term stability, wear and fatigue issues.

Such conventional methods and systems have generally been considered satisfactory for their intended purpose. However, there is still a need in the art for artificial valves that allow for improved fatigue resistance. There also remains a need in the art for such artificial valves that are easy to make and use. The present invention provides a solution for these problems.

SUMMARY OF THE INVENTION

The subject invention is directed to new and useful artificial valves. The applications incorporated by reference above generally provide mechanical design details. This application is more particularly directed to the issues of valve material compatibility, stability and durability by material selection and manufacturing techniques used to address the specific requirements of fatigue related to the imbalance of stresses between metal parts and elastic polymer components, by:

Selecting optimal, proven materials designed to perform in this harsh environment,
Reducing stress concentrations at the interfaces between materials having radically different stiffness and modulus of elasticity,
Reducing friction between component joints, and
Increasing tear resistance of the polymer components.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the apparatus of subject invention without undue experimentation, preferred embodiments thereof will be described in detail hereinbelow with reference to certain figures, wherein:

FIG. 12 is a front elevation view of the flow-regulating device of FIG. 9, showing the membrane or sail in place;

FIG. 13 is a side elevation view of the flow-regulating device of FIG. 12, showing one of the symmetrical x-shaped linking members connecting the two axially spaced apart ring portions with the membrane or sail attached to a portion of the cross members of the x-shaped linking member; and FIG. 14 is a perspective view of the flow-regulating device of FIG. 12, showing both of the x-shaped linking members with the membrane or sail in place in the flow restricting position.

DETAILED DESCRIPTION OF THE PREFERRED EMBODIMENTS

Figure 1:
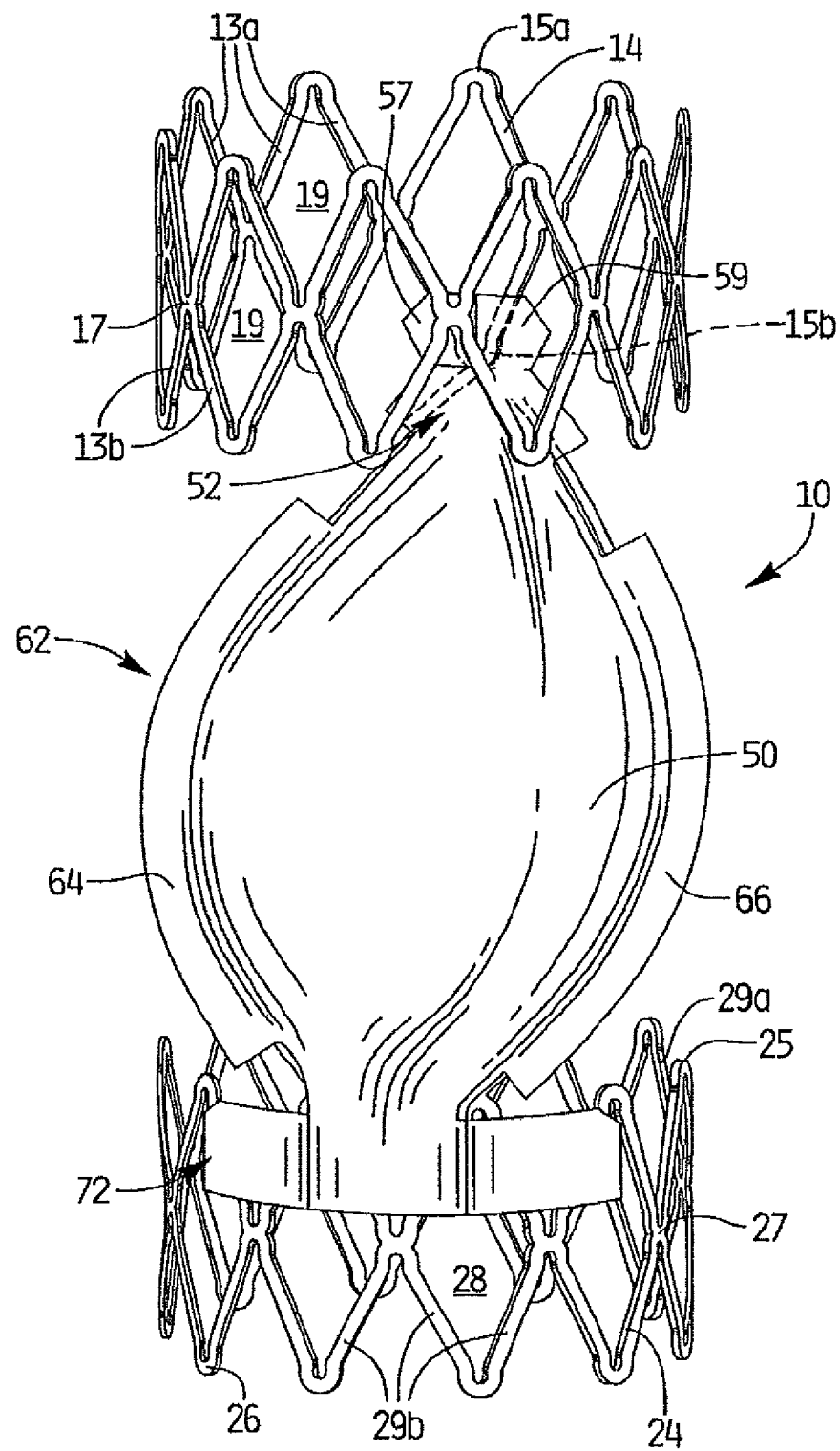
FIG. 1 is a perspective view of the flow regulating device of the present invention, prior to full assembly.

Reference will now be made to the drawings wherein like reference numerals identify similar structural features or aspects of the subject invention. For purposes of explanation and illustration, and not limitation, a partial view of an exemplary embodiment of an artificial valve in accordance with the invention is shown in FIG. 1 and is designated generally by reference character 10. Other embodiments of valves in accordance with the invention, or aspects thereof, are provided in FIGS. 2-14, as will be described. The system of the invention can be used to improve performance and manufacturing of artificial valves.

Regulating device 10 includes an elongated support 12 that has upper and lower substantially annular ring portions 14 and 24, each having a series of rounded V-shaped apices 15a facing in an upward direction and a series 15b facing in a downward direction. That is, the upper or distal (with respect to the direction of blood flow) ring portion 14 has a first series of angled struts 13a forming a V and a second series of angled struts 13b forming an inverted V which together form a group of closed substantially diamond shaped cells 19 connected at region 17. Similarly, the lower or proximal (with respect to the direction of blood flow) ring portion 24 has a first series of angled struts 29a and a second series of angled struts 29b, facing in opposite directions and forming closed substantially diamond shaped cells 28 connected at region 27. The cells 28 have upper apices 25 and lower apices 26. For clarity, not all of the identical parts in the drawings are labelled. Note that in the preferred embodiment, the rings and linking member (described below) are preferably integral so that terms "joined", "connected", etc. are used for ease of description.

Figure 2:
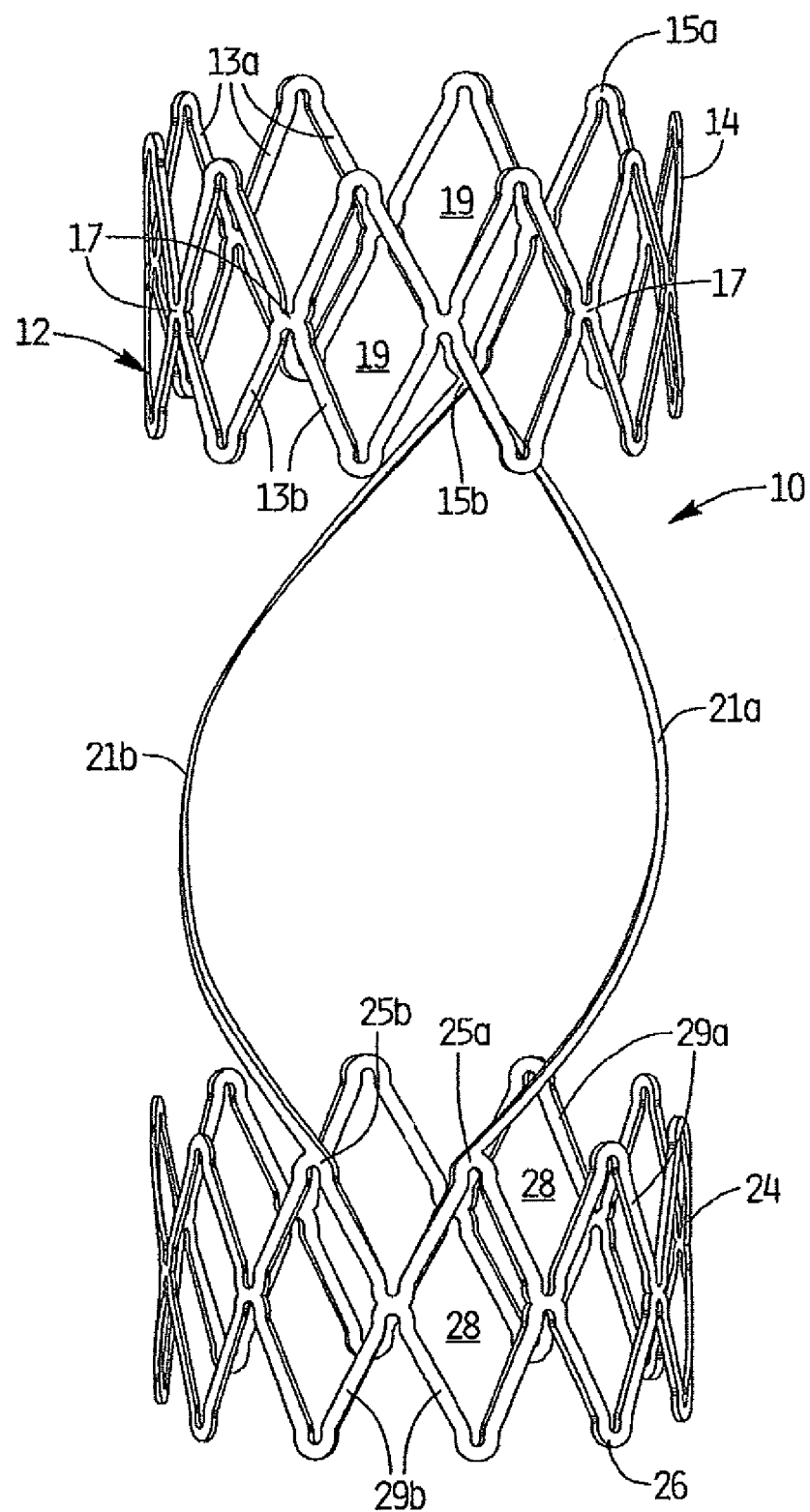
FIG. 2 is a perspective view of the support of the flow-regulating device of FIG. 1.

Support 12 has two curved linking or connecting members 21a, 21b, best shown in FIG. 2 in which the membrane is removed for clarity. The top of each connecting member 21a, 21b extends from a common lower apex 15b of one of the pairs of angled struts 13b of upper ring 14 (see also FIGS. 3 and 4) The lower end of connecting members 21a, 21b extend from separate upper apices 25a, 25b, respectively, of cells 28 of lower ring 24. In the illustrated embodiment, the apices 25a, 25b, are about 36 degrees apart as ten cells are formed. However, a different number of cells can be provided with different spacing between apices. Also, it should be appreciated that the connecting members can extend from other apices of lower ring 24 or upper ring 14. The connecting members 21a, 21b have a curve or twist extending close to about 180 degrees (and extending substantially across the vessel when implanted) so that an upper end is connected to one end (viewed radially/transversely) of the device 10 and the lower end is connected to an opposite end (viewed radially/transversely) of the device 10. That is, with ten closed cells in the illustrated embodiment, apex 15b is approximately 162 degrees out of phase from apex 25a and from apex 25b. Other spacing and alternate number of cells is also contemplated.

Although two connecting members are shown, one connecting member or more connecting members could be provided. Also, the connecting members could be spaced further or closer apart and have different curves than shown.

The rings 14, 24 are collapsed to a reduced diameter (profile) position for delivery. The rings 14, 24, when implanted, are substantially perpendicular to the direction of blood flow. Preferably, the rings 14, 16 in their expanded (deployed) configuration are larger in diameter than the internal diameter of the target vessel to apply a sufficient radial force against the vessel to ensure that the device remains in a desired position and orientation after implantation. For example, for use in an 8 mm vessel, the rings could have an expanded outer diameter of about 10 mm and preferably could be collapsed sufficiently to be delivered through a 12 Fr (4 mm) delivery catheter. Others ring diameters are also contemplated.

The support 12 is preferably composed of shape memory material, such as Nitinol or Elgitoy, with a shape memorized larger diameter configuration as shown in the drawings. In the illustrated embodiment, the support is laser cut from a tube so that the connecting members and rings are integral. However, it is also contemplated that alternatively the support can be formed from wire(s). Also, it should be appreciated that instead of being integral, separate members could be provided, with separate rings joined by separate linking (connecting) members.

Device 10 includes a valve member or membrane 50 that is operatively associated with support 12 for regulating the flow of blood through a vessel by moving between open and closed positions. Membrane 50 is preferably formed from a sheet of ultra thin membrane material such as a ePTFE material or the like. It is envisioned that the membranes disclosed herein could be bonded or otherwise coated with an anti-blotting or anti-coagulant/anti-thrombogenic agent such as Heparin and/or an anti-proliferative coating, to retard the body's desire to reject the implant. In a preferred embodiment, the membrane is coated with an anti-thrombogenic agent and the frame is coated with an anti-proliferative agent, such as Dexamethasone by way of example.

Figure 3:
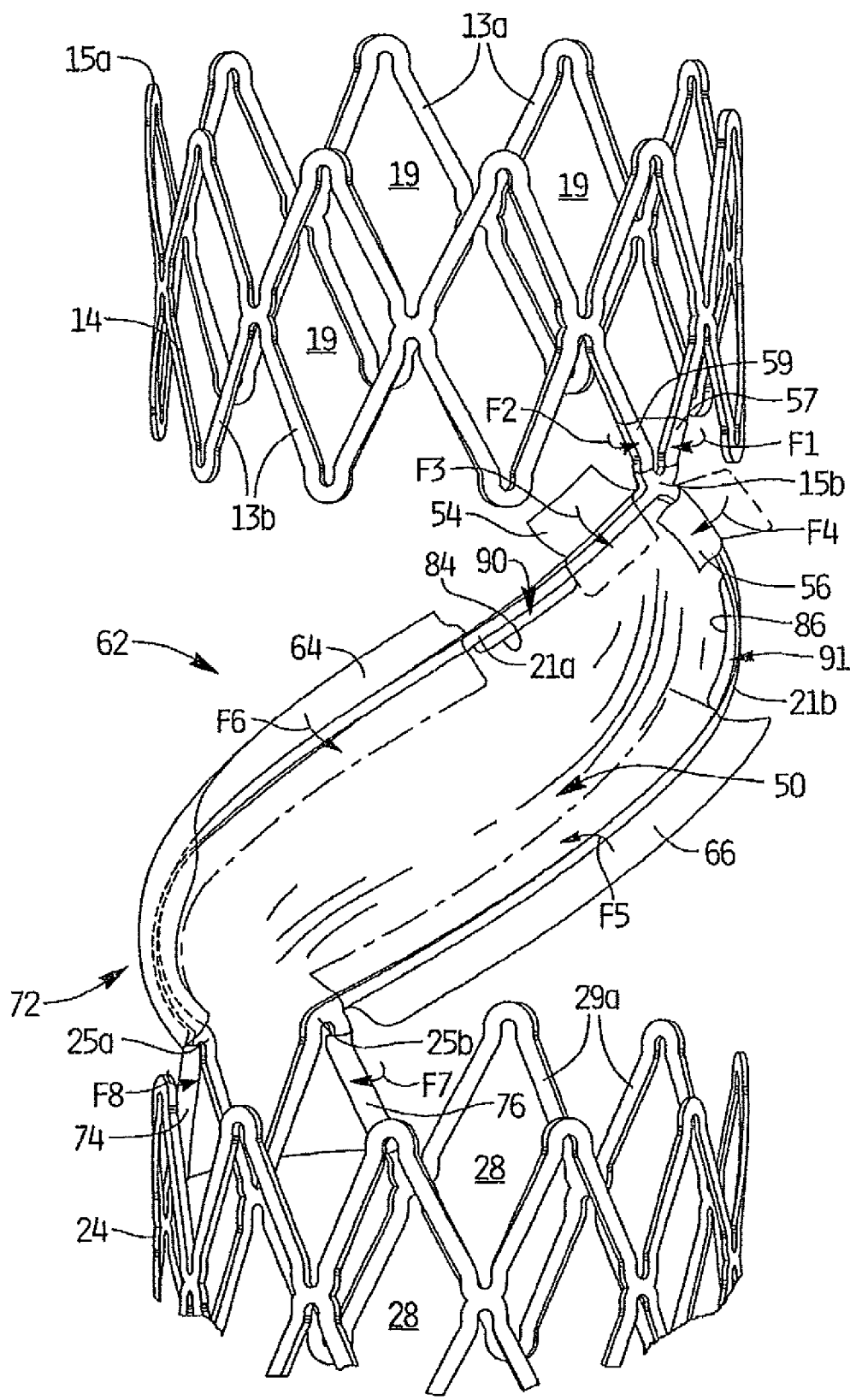
FIG. 3 is a side perspective view of the flow regulating device illustrating how the membrane is attached to the frame.
Figure 4:
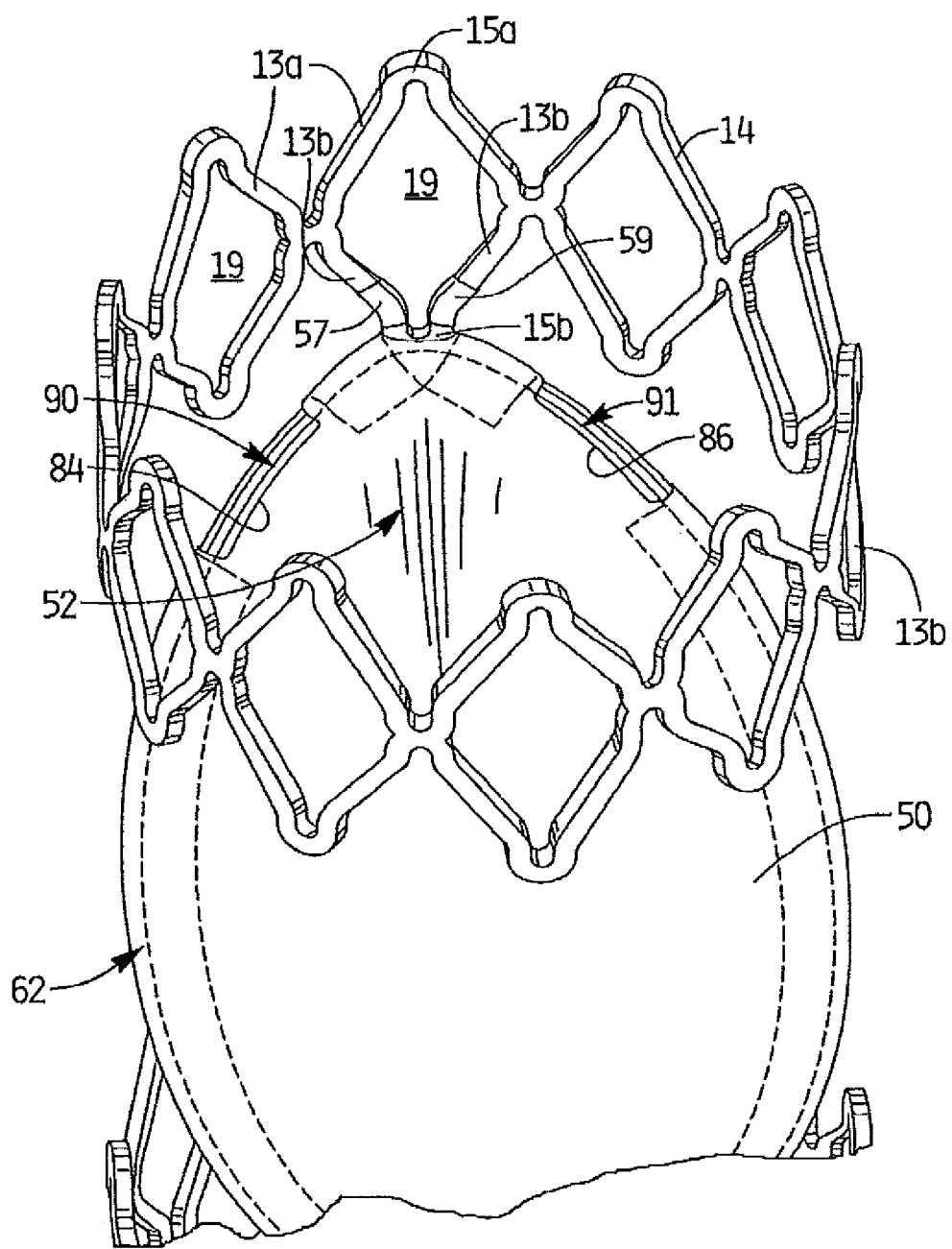
FIG. 4 is a front perspective view of the top (distal) portion of the flow regulating device of FIG. 1 showing the membrane in the closed position.

As shown, valve membrane 50 has an upper portion 52, an intermediate portion 62, and a lower portion 72. With reference to FIG. 3 which illustrates how the membrane 50 is attached to support 12 in manufacture, the top portion 52 has first and second flaps 54, 56 which are folded down over respective connecting members 21a, 21b and attached to the membrane to secure the upper portion 52 of membrane 50 about the support 12. FIG. 3 illustrates flap 56 already folded in the direction of arrow F4 from its unfolded position shown in phantom. FIG. 3 also illustrates flap 54 in its unfolded position before movement in the direction of arrow F3 in manufacture to its folded position depicted in phantom. Flaps 57 and 59 at the uppermost region of membrane 50 are wrapped around struts 13b in the direction of arrows F1, F2, respectively.

With continued reference to FIG. 3, the intermediate portion 62 of membrane 50 has flaps 64, 66 for connection to linking (connecting) members 21a, 21b, respectively. Flap 64 is shown in a mostly unfolded position to be folded in the direction of arrow F6 to its folded position shown in phantom where it is attached to the membrane 50. Flap 66 is shown in its unfolded position to be folded in the direction of arrows F5 to its folded position depicted in phantom.

Lower portion 72 of membrane 50 has flaps 74 and 76 which are each folded around a separate strut 29a. Arrows F8, F7, respectively, illustrate the direction of the fold.

Cuts in the membrane 50 create an unattached flap 84 between upper attached flap 54 and intermediate attached flap 64 and an unattached flap 86 between upper attached flap 56 and intermediate attached flap 66. These unattached flaps 84, 86 are positioned adjacent the respective connecting member 21a, 21b as shown, but create a respective opening 90, 91 for blood flow between the membrane 50 and connecting members 21a, 21b as described below. Note, alternatively, the flaps 84, 86 can extend over the connecting member, as long as it remains unattached and creates a sufficient space from the linking member to create a sufficiently sized opening to allow blood flow therethrough.

Note that FIG. 1 shows the membrane 50 with the flaps open, prior to connection in manufacture, to illustrate how it is wrapped around the support 12 and connected to other portions of the membrane for securement/attachment of the membrane to the support 12. The flaps, after wrapping over/around the region of support 12, can be connected to the membrane body by welding, adhesive, suturing or other methods. Also, an intermediary material can be used to facilitate welding, such as polyurethane or polycarbonate/polyurethane impregnated or otherwise combined with the ePTFE material. It is also contemplated that the membrane can be attached to the support 12 itself by methods such as by adhesive or use of suture material.

Figure 6A:
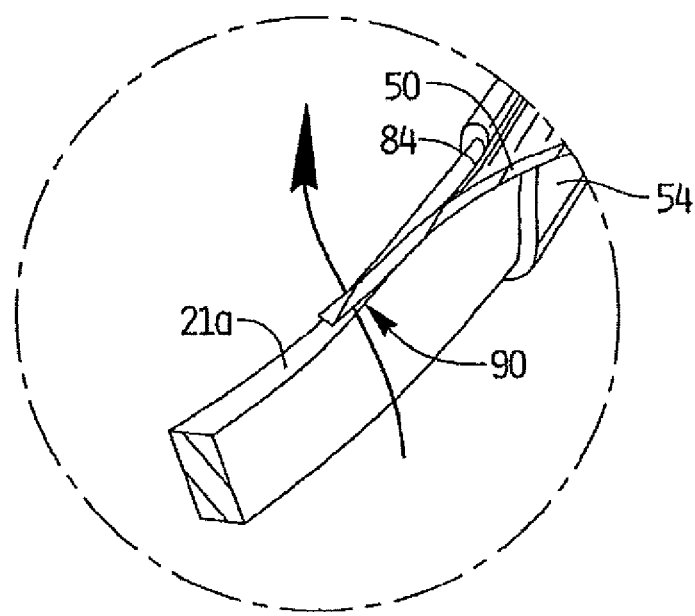
FIG. 6A is a cross-sectional view of the identified area of FIG. 5A showing the membrane in the open position, resulting from antegrade blood flow.
Figure 6B:
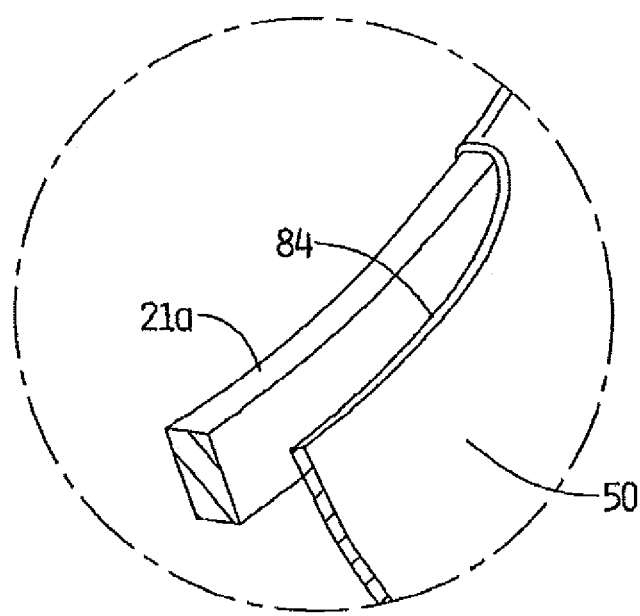
FIG. 6B is a cross-sectional view of the identified area of FIG. 6A showing the membrane in the closed position, resulting from retrograde blood flow.
Figure 6C:
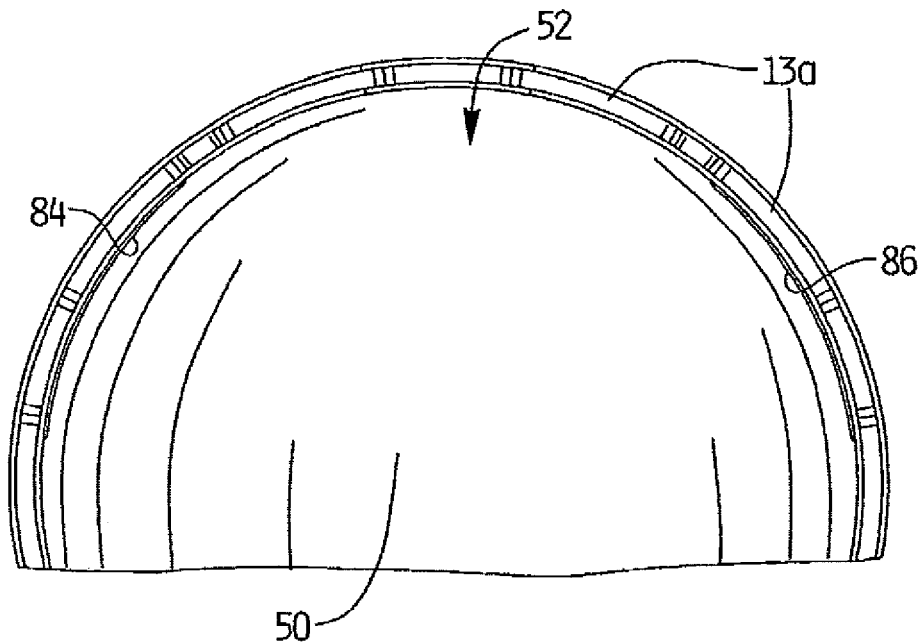
FIG. 6C is a top view of the upper region of the membrane of FIG. 5B showing the membrane in the closed position.
Figure 6D:
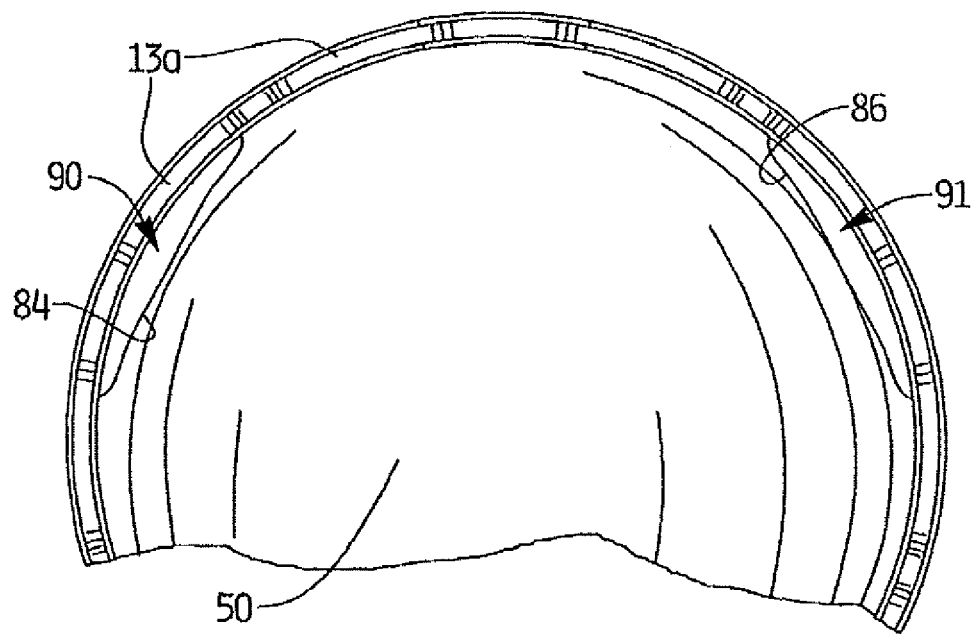
FIG. 6D is a top view of the upper region of the membrane of FIG. 5A showing the membrane in the open position.
Figure 6E:
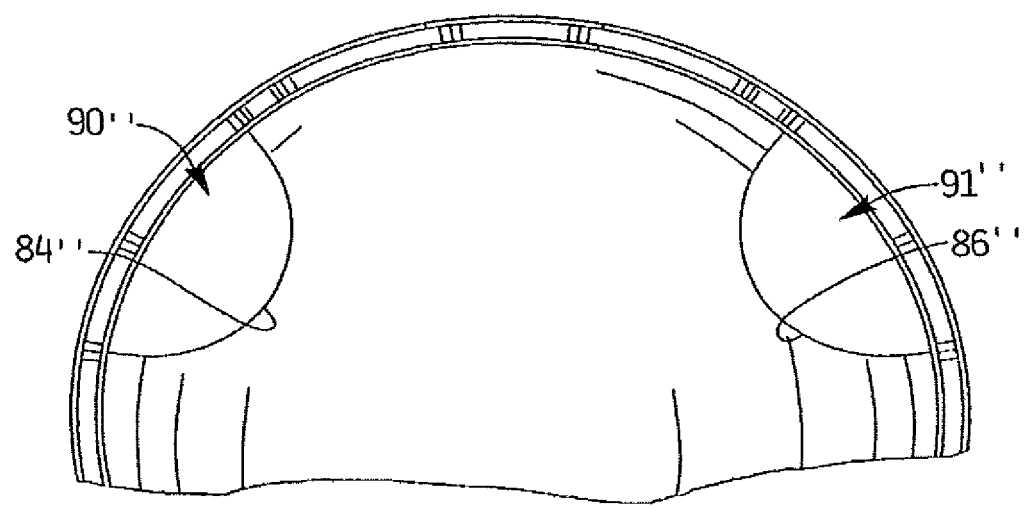
FIG. 6E is a top view of the upper region of another exemplary embodiment of the membrane shown in the open position.
Figure 7A:
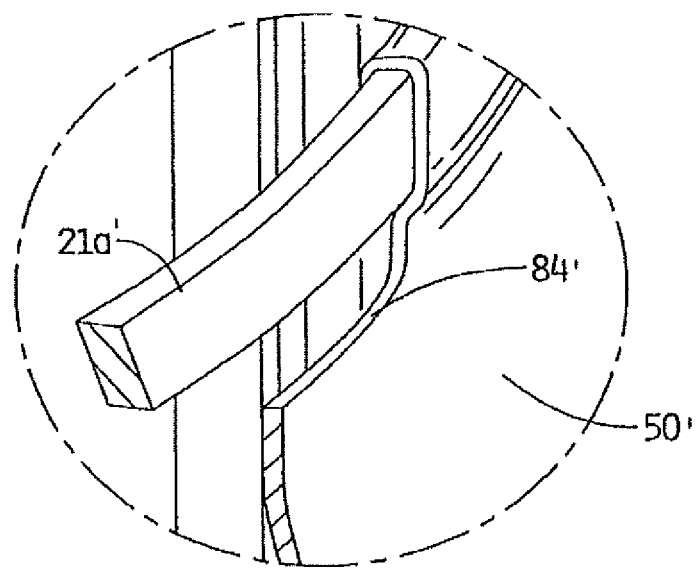
FIG. 7A is a cross-sectional view similar to FIG. 6B except showing the membrane of FIG. 7 in the closed position.
Figure 7:
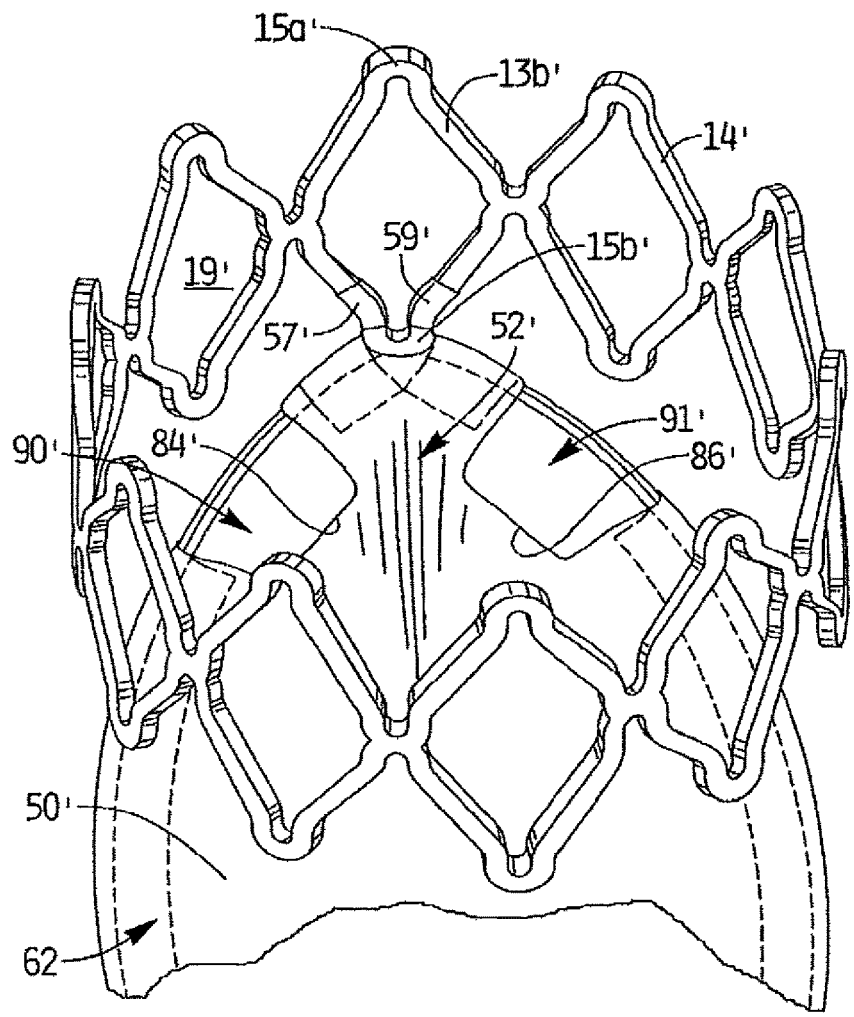
FIG. 7 is a view similar to FIG. 4 showing another exemplary embodiment of the membrane with flaps forming larger openings for increased antegrade blood flow.

As can be appreciated, the body portion of the membrane 50 extends substantially if not entirely across the expanse of the vessel in the open position. However, the openings 90 and 91 adjacent the unattached flaps 84, 86 provide a sufficient gap for the necessary amount of blood flow, it being appreciated by applicants that a normally functioning valve is only open about 35%. In some embodiments, the openings in the membrane created by the space between flaps 84, 86 and the support create a space gap in the range of about 5% to about 15% of the diameter of the vessel. In the alternate embodiment depicted in FIG. 7, larger openings 90' and 91' are formed to allow more antegrade blood flow. In these large opening embodiments, a space (opening) can be created preferably representing about 15% to about 45%, and more preferably from about 15% to about 30% of the diameter of the vessel. (In all other respects the regulating device of FIG. 7 is identical to that of FIG. 4 and the corresponding parts are labelled by numerals with a prime designation and therefore are not discussed herein). These percentages are defined in terms of the diameter of the blood vessel. For example, if a rectangular opening is formed of dimension of 2 mm×4 mm, and is placed in a 10 mm vessel, the cross section occupied by the two openings (about 16 mm) would be about 20% of the overall diameter of the vessel (about 78 mm). It should be appreciated that the foregoing ranges and percentages are provided by way of example and other size openings creating a different percentage opening are also contemplated. Also, other shape openings can be provided other than rectangular, including square, semicircular, etc. FIG. 6E shows by way of example substantially semicircular openings 90", 91" formed by flaps 84", 86", respectively.

Figure 5A:
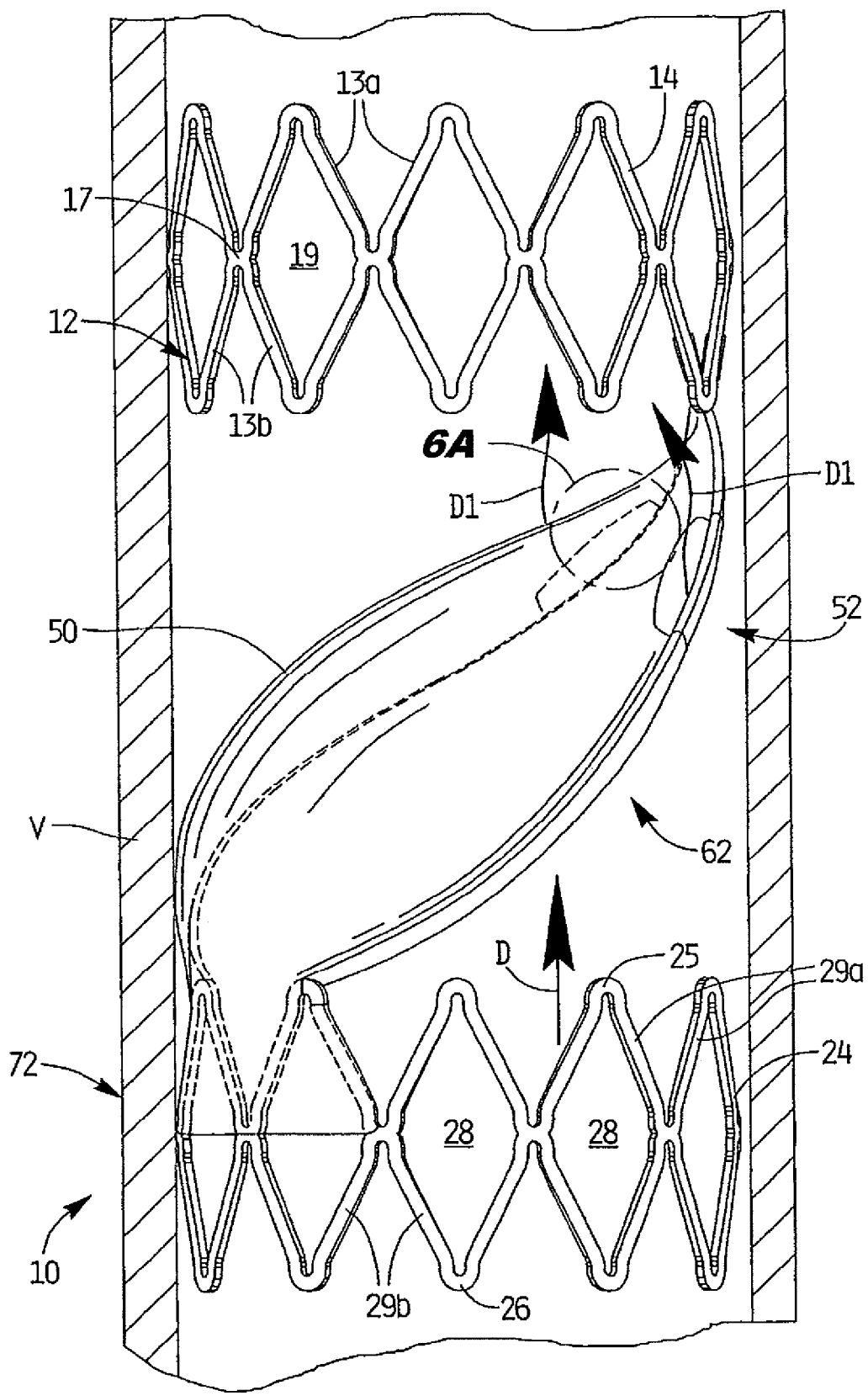
FIG. 5A is a side perspective view showing the membrane in the open position.
Figure 5B:
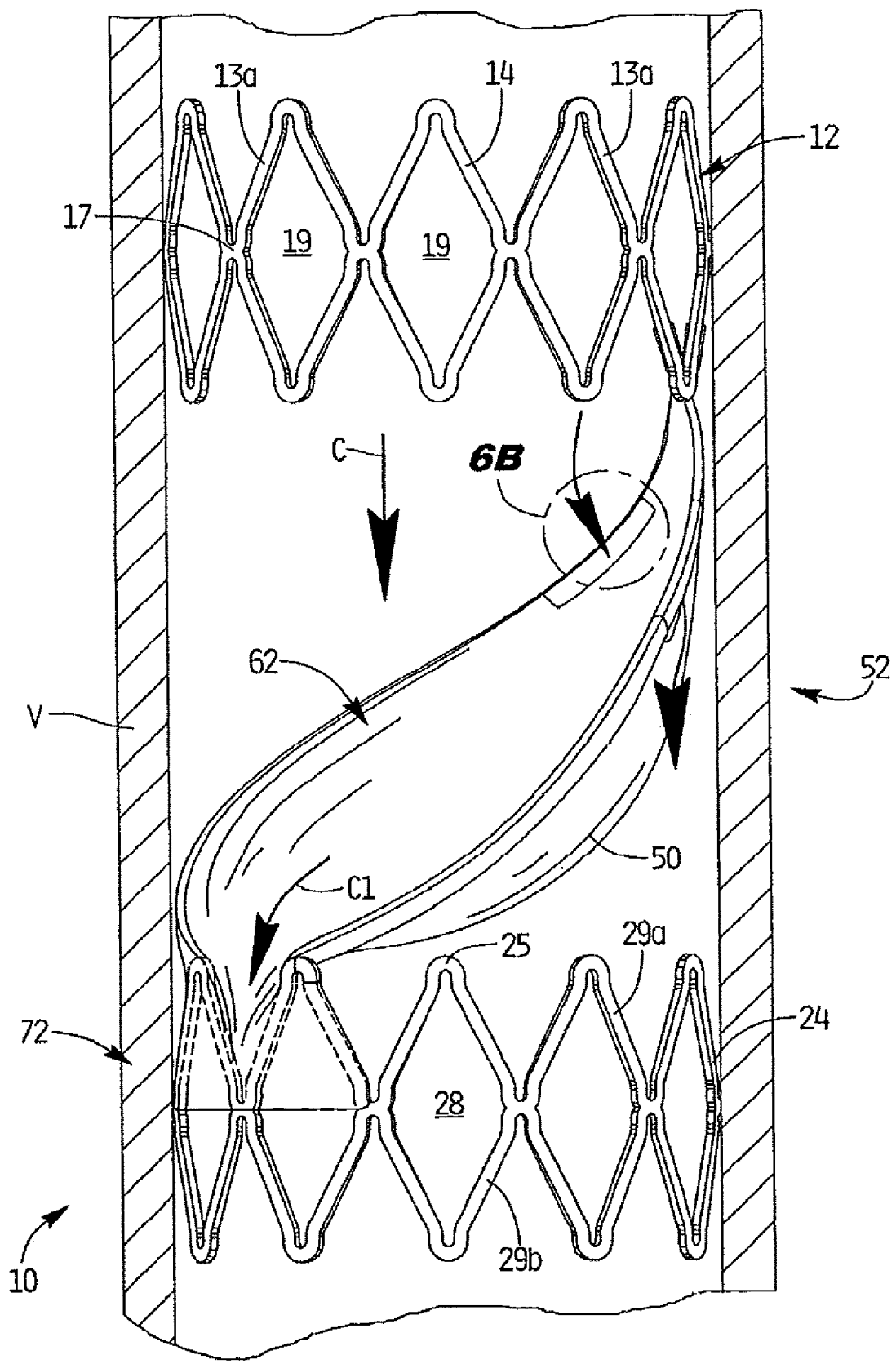
FIG. 5B is a side perspective view similar to FIG. 5A showing the membrane in the closed position.

Movement of the membrane 50 between an open (blood flow enabling) position/condition to allow antegrade blood flow and a closed (blood flow inhibiting position/condition) to essentially block flow are shown in respective FIGS. 5A and 5B, and shown in more detail in FIGS. 6A-6D. In the closed position, however, a minimal amount of blood flow is allowed as will be discussed below.

More specifically, and with reference to FIG. 5A, blood flowing through the blood vessel V in the downstream direction (antegrade flow) indicated by arrow "D" will act against the valve membrane 50 in such a manner as to push the body portion upwardly as viewed in the drawing, creating a concave belly on the underside. The blood will travel along the concave surface and up the membrane and the blood pressure will force the flaps 84 and 86 upwardly, separating (spreading) them from the respective connecting members 21a, 21b as also shown in FIGS. 6A and 6D to form an opening or gap.

After the pulsed blood travels in the direction of arrow D1 (FIG. 5A), through the openings (spaces) 90, 91, the blood backs up in the direction of arrow C of FIG. 5B. This retrograde blood flow will act against the angled body of the membrane 50, forcing it downwardly as viewed in FIG. 5B to form a convexity on its underside. This downward pressure will force flaps 84, 86 downwardly adjacent to the connecting members 21a, 21b, respectively, and against the connecting member as shown for example in FIGS. 6B and 6C, thus essentially closing the openings 90, 91 to prevent blood flow therethrough. However, a small amount of blood will force its way between the membrane 50 and the vessel wall as depicted by arrow C1 in FIG. 5B, thereby reducing stasis or stagnation that could lead to clotting. In embodiments wherein a larger flap is utilized to create a larger opening, such as in the embodiment of FIG. 7, the flap 84' (and 86', not shown) in the closed position would lie adjacent the connecting members, and extend underneath the connecting member (e.g. connecting member 21a') to lie against the vessel wall as shown in FIG. 7A, thereby inhibiting blood flow.

It should be appreciated that the membrane extends at an angle across the vessel of about 50 to about 70 degrees to help direct the blood flow and continuously wash the membrane body to prevent blood stagnation. (Other angles are also contemplated) More specifically, blood contacting the body portion of the membrane 50 in the open position will be directed upwardly, along the concave surface, thereby washing the membrane body to wash away clots to reduce the likelihood of clotting. In the closed position, blood contacting the membrane body will be directed downwardly along the angled body to wash the opposing side of the membrane to likewise reduce the likelihood of clotting.

As can be appreciated, the membrane 50 remains at substantially the same angle across the blood vessel in the open (flow allowing) and closed (flow inhibiting) positions/conditions. That is, as shown in FIGS. 5A and 5B, the upper region of the membrane 50 is adjacent one side of the vessel wall in the open (flow allowing) position. The upper region remains adjacent the same wall in the closed (flow inhibiting) position. Similarly, the lower region of the membrane 50 is adjacent an opposite side of the vessel wall, and remains adjacent that wall in both the open and closed positions of FIGS. 5A, 5B, respectively. Thus, the upper and lower attached regions of the membrane remain in substantially the same position.

Figure 8:
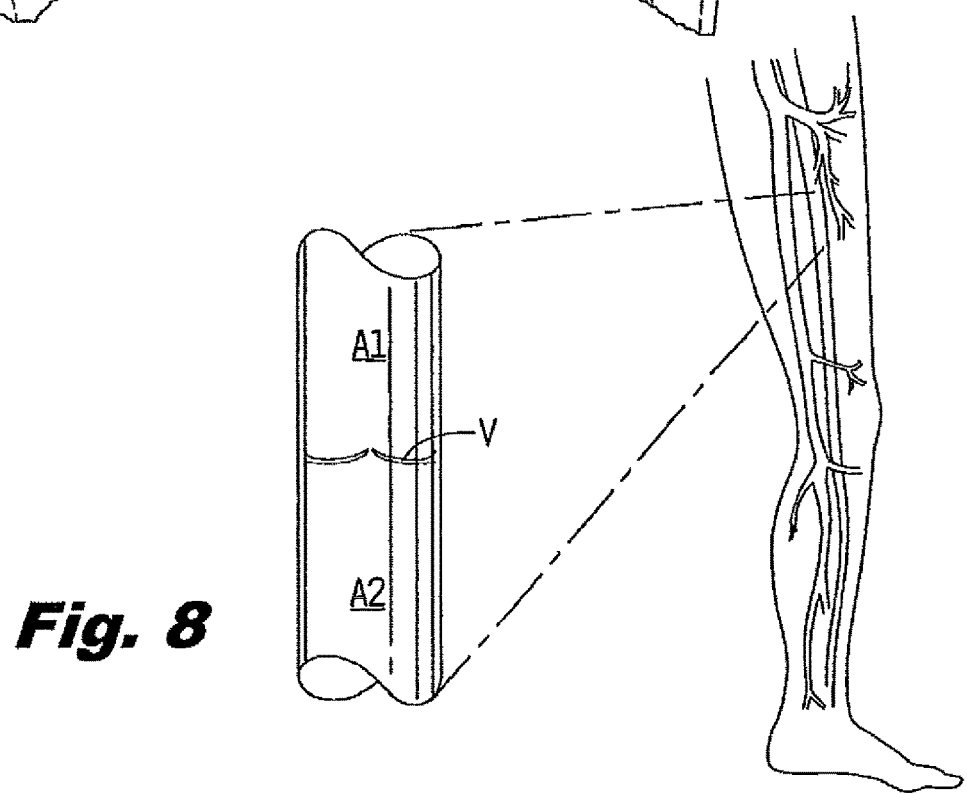
FIG. 8 is a drawing of the anatomy of the patient showing two examples of locations of placement of the flow regulating device.

One example of the location of placement of the flow regulating device in a patient's leg is shown in FIG. 8 with areas A1 and A2 showing possible placement sites of the device, e.g. upstream or downstream of the native valve V.

If composed of shape memory, the device will automatically expand to the position shown either upon release from a delivery member or in response to temperature change. However, if composed of other materials, the device can be designed to automatically expand due to the springiness of the material or can alternatively be implanted in a blood vessel using a balloon catheter (not shown) as described in copending U.S. patent application Ser. No. 11/801,691, the entire contents of which are incorporated herein by reference. That is, rings 14 and 24 can be moved from a closed position to an expanded position by inflating the balloon or by use of a mechanical expander. Upon expansion, the rings 14 and 24 apply a force against the vessel wall, thereby being retained therein. The balloon or mechanical expander is then deflated and the catheter is removed from the blood vessel so the device 10 can regulate the flow of blood through the vessel in the manner described above.

In the embodiments disclosed herein showing substantially circular rings, it should be understood that the rings can be shaped to have a size larger than the diameter of the vessel and therefore, depending on the size of the vessel, may not assume a circular shape but have an oval shape pressing against the vessel wall toward a circular configuration.

Figure 9:
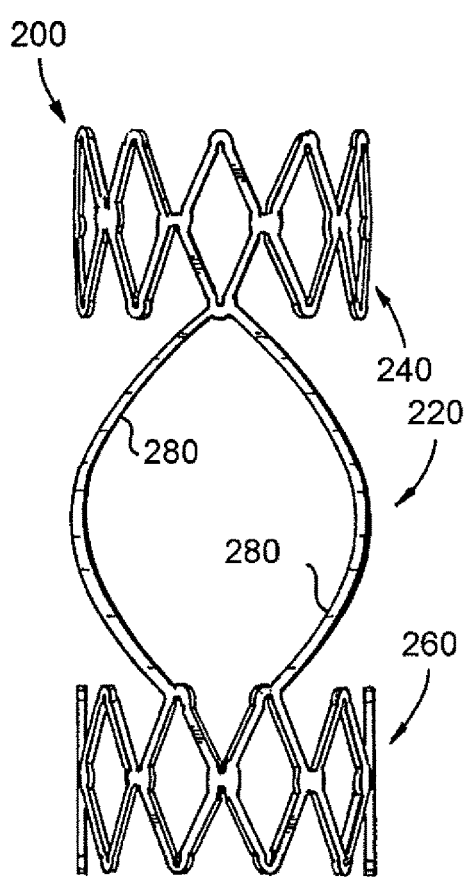
FIG. 9 is a front elevation view of the frame of a flow-regulating device constructed in accordance with another embodiment of the subject invention with the membrane or sail removed for clarity.
Figure 10:
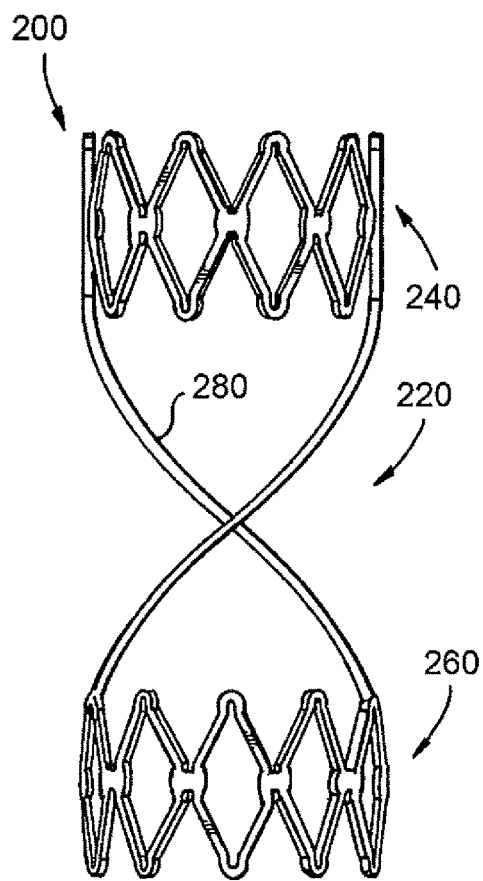
FIG. 10 is a side elevation view of the frame of FIG. 9, showing one of the symmetrical x-shaped linking members connecting the two axially spaced apart ring portions.
Figure 11:
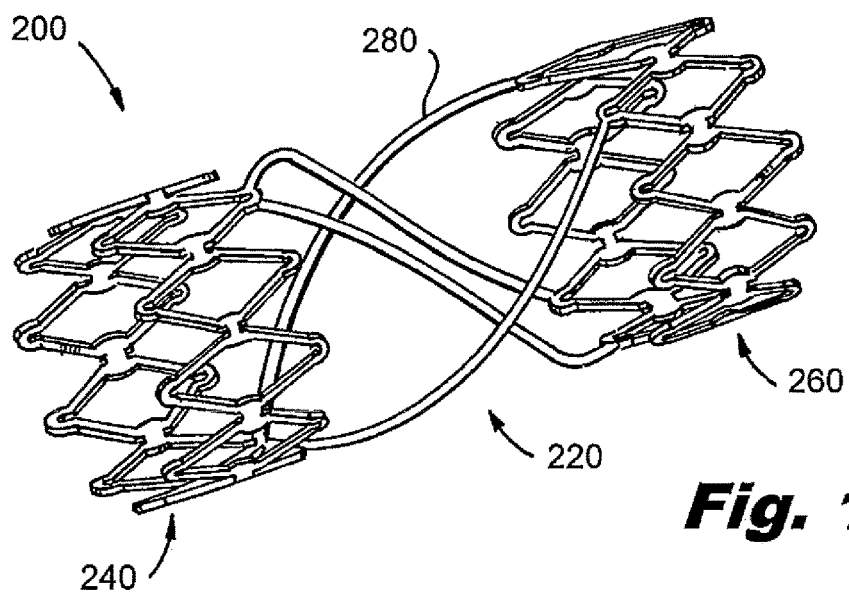
FIG. 11 is a perspective view of the frame of FIG. 9, showing both of the symmetrical x-shaped linking members.

Referring now to FIGS. 9-11, there is shown a frame for a flow regulating device constructed in accordance with another preferred embodiment of the subject invention, and designated generally by reference numeral 200. Regulating device 200 includes an elongated frame 220 that consists of upper and lower substantially annular ring portions 240 and 260, much as described above. Rings 240 and 260 are connected to one another by at least one connective member 280 in the form of an x-shaped bar or wire. In the exemplary embodiment of FIGS. 9-14, two x-shaped connective members 280 are shown. Connective members 280 are adapted and configured to follow the circumference of the host vessel. The individual cross-linked bars or wires of each x-shaped connective member 280 are attached to the opposed rings 240 and 260 of frame 220 at locations that are about 180° apart from one another, making device 200 substantially symmetrical. This gives frame 220 an inherent symmetrical flexibility and enables it to move with the natural movements (e.g., pulsitile) of the vein.

FIGS. 12-14 show device 200 with the membrane, much as described above, in place. Membrane or sail 250 attaches to portions of the x-shaped connective members 280. Apertures 270 allow blood flow in one direction, and inhibit flow in the opposite direction much as described above. This frame and sail configuration gives device 200 more support and symmetry, allows for delivery using a simpler delivery device, distributes stress more evenly and reduces stress raisers between support portions.

The frame, described in the above and in the applications incorporated by reference above, can be made of a laser cut, heat set, smoothly micro-polished one piece Nitinol construct, a well known and well tolerated super elastic alloy, used for many years in the vasculature and more recently proven to be successfully implanted within the target valve anatomical location. See, e.g., Neglen et al, Journal of Vascular Surgery November 2007, which is incorporated by reference herein in its entirety.

The valve membrane or leaflet, as described above and in the applications incorporated by reference above, can be manufactured from an ePTFE (expanded polytetrafluoroethylene), which is a material with a long history of being well tolerated in the vasculature. This ePTFE leaflet is designed and built to have specific stress relieved and annealed characteristics and specific porosity designed to allow attachment and adherence of the attachment polymer, while maintaining the mechanical, functional, stability and biocompatibility requirements for this specific application, as described in further detail below.

The practical assembly of this device is based on a unique heat shaping process of the leaflet material combined with the micro thin application and impregnation of a proven biocompatible polycarbonate polyurethane material to the underside with respect to the orientation of FIG. 3 of the leaflet in the seam area enabling the application of heat to seamlessly attach the leaflet to the frame, via the folding described above and in the applications incorporated by reference above.

These attachment techniques allow the polymer material to be attached to the frame without any perforation of the leaflet material (perforations of a thin polymer sheet under frequent cyclic movement lead to the potential for accelerated risk of tear propagation of the polymer sheet, as demonstrated in other medical device applications where tears were seen at suture hole locations after cyclical use).

The folding processes described above and in the applications incorporated by reference above can additionally include some or all of the following:

1. Spraying the metal frame of the valve with silicone lubricant, to prevent adherence of the leaflet to the frame through the heat-welding process;

2. Wrapping the leaflet around the frame and welding of the leaflet material to itself, forming a continuous flexible seam around the metal frame, without the leaflet material being adhered to the frame;

3. Using a pre-shaped bi-axially stress relieved and annealed ePTFE material with the porosity range selected between 15 and 25 microns, these size pores are large enough to allow deep and uniform penetration of a Polycarbonate polyurethane adhesive, and/or other suitable adhesive, into the bulk of the leaflet; but small enough to prevent blood seepage through the leaflet;

4. Forming the leaflet from a thermally-fitted and fully annealed polymer sheet, reducing the risk of folds and creases in the leaflet that could harbor cellular adherence;

5. Melting the thinly applied and impregnated Polycarbonate polyurethane (the strongest and most flexible of the polyurethane elastomers), to smooth out the seam making it virtually invisible, reducing the potential for blood or cellular adherence; and 6. Using a pre-programmed laser cutting apparatus, and/or other suitable device, to cut out openings in the leaflet, to allow blood flow though the valve, as described in the applications incorporated by reference above. Laser cutting of the leaflet material causes the cut edge to be sealed and lowers the risk of the cut edge having the potential for tearing or ripping during use.

The methods and systems of the present invention, as described above and shown in the drawings, provide for flow regulating devices with superior properties including fatigue resistance, biocompatibility, and ease of manufacture. While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. A method of making an implantable device for regulating blood flow through a blood vessel, comprising:
   a) forming an elongated support dimensioned and configured to be implanted in a blood vessel, the support including axially spaced apart first and second substantially annular support portions, and a linking member linking the axially spaced apart portions to one another;

b) forming a valve membrane configured for extending between the axially spaced apart support portions, the valve membrane including a first region, a second region, and a flap adjacent the first region, and the second region being adjacent the first region and configured to be unattached to the linking member and movable between a first position to enable blood flow and a second position to inhibit blood flow;

c) folding the flap over the linking member for attachment to the first region of the valve membrane for attachment of the valve membrane to the linking member;

d) impregnating at least one of the flap and the first region of the valve membrane with an impregnation material;

e) joining the flap substantially seamlessly to the first region of the valve membrane by heat shaping at least one of the flap and the first region to form an adhesion region joining the flap and the first region together, wherein the adhesion region includes the impregnation material; and f) spraying the support with silicone lubricant, to prevent adherence of the valve membrane to the support during the joining step.

2. A method of making an implantable device for regulating blood flow through a blood vessel, comprising:

a) forming an elongated support dimensioned and configured to be implanted in a blood vessel, the support including axially spaced apart first and second substantially annular support portions, and a linking member linking the axially spaced apart portions to one another;

b) forming a valve membrane using a pre-shaped bi-axially stress relieved and annealed ePTFE material with the porosity range selected between 15 and 25 microns and configured for extending between the axially spaced apart support portions, the valve membrane including a first region, a second region, and a flap adjacent the first region, and the second region being adjacent the first region and configured to be unattached to the linking member and movable between a first position to enable blood flow and a second position to inhibit blood flow, wherein the valve member comprises c) folding the flap over the linking member for attachment to the first region of the valve membrane for attachment of the valve membrane to the linking member;

d) impregnating at least one of the flap and the first region of the valve membrane with an impregnation material;

e) joining the flap substantially seamlessly to the first region of the valve membrane by heat shaping at least one of the flap and the first region to form an adhesion region joining the flap and the first region together, wherein the adhesion region includes the impregnation material.

3. A method as recited in claim 2, wherein the support is formed at least in part from a one piece Nitinol construct.

4. A method as recited in claim 2, wherein the impregnation material includes a biocompatible polycarbonate polyurethane material.

5. A method as recited in claim 2, wherein the folding and joining steps include wrapping the flap around the support and welding of the valve membrane material to itself at the flap and first region, and forming a continuous flexible seam around the support, without the valve membrane being adhered to the support.

6. A method as recited in claim 2, wherein the step of joining includes melting the impregnation material to smooth out the adhesion region making the adhesion region substantially seamless, reducing potential for blood or cellular adherence thereto.

7. A method of making an implantable device for regulating blood flow through a blood vessel, comprising:

a) forming an elongated support dimensioned and configured to be implanted in a blood vessel, the support including axially spaced apart first and second substantially annular support portions, and a linking member linking the axially spaced apart portions to one another;

b) forming a valve membrane configured for extending between the axially spaced apart support portions, the valve membrane including a first region, a second region, and a flap adjacent the first region, and the second region being adjacent the first region and configured to be unattached to the linking member and movable between a first position to enable blood flow and a second position to inhibit blood flow, wherein the step of forming the valve membrane includes using a pre-programmed laser cutting apparatus to cut out openings in the valve membrane for allowing blood flow though the implantable device;

c) folding the flap over the linking member for attachment to the first region of the valve membrane for attachment of the valve membrane to the linking member;

d) impregnating at least one of the flap and the first region of the valve membrane with an impregnation material;

e) joining the flap substantially seamlessly to the first region of the valve membrane by heat shaping at least one of the flap and the first region to form an adhesion region joining the flap and the first region together, wherein the adhesion region includes the impregnation material.

\* \* \* \* \*